US011497473B2

(12) United States Patent
Salles et al.

(10) Patent No.: US 11,497,473 B2
(45) Date of Patent: Nov. 15, 2022

(54) ULTRASOUND CARDIAC PROCESSING

(71) Applicant: Norwegian University of Science and Technology (NTNU), Trondheim (NO)

(72) Inventors: Sebastien Salles, Trondheim (NO); Lasse Lovstakken, Trondheim (NO); Hans Torp, Trondheim (NO)

(73) Assignee: Norwegian University of Science and Technology (NTNU), Trondheim (NO)

( * ) Notice: Subject to any disclaimer, the term of this patent is extended or adjusted under 35 U.S.C. 154(b) by 244 days.

(21) Appl. No.: 16/585,034

(22) Filed: Sep. 27, 2019

(65) Prior Publication Data

US 2021/0085294 A1 Mar. 25, 2021

(30) Foreign Application Priority Data

Sep. 20, 2019 (GB) ..................................... 1913624

(51) Int. Cl.
*A61B 8/08* (2006.01)
*G06T 15/08* (2011.01)
(Continued)

(52) U.S. Cl.
CPC .............. *A61B 8/485* (2013.01); *A61B 5/318* (2021.01); *A61B 8/0883* (2013.01);
(Continued)

(58) Field of Classification Search
CPC ......... A61B 5/318; A61B 8/488; A61B 8/483; A61B 8/0883; G06T 15/08
See application file for complete search history.

(56) References Cited

U.S. PATENT DOCUMENTS 5,622,174 A * 4/1997 Yamazaki ............... A61B 8/463
600/455
8,094,893 B2 * 1/2012 Roundhill ........... G01S 15/8979
382/128

(Continued)

FOREIGN PATENT DOCUMENTS

WO 2014/049346 4/2014
WO 2018/154109 8/2018

OTHER PUBLICATIONS

Salles, Sebastien, et al. "Natural Mechanical Wave Detection Using Ultrafast Ultrasound and Velocity Clutter Filter Wave Imaging." *Archive Ouverte HAL*, Apr. 9, 2019, https://hal.archives-ouvertes.fr/hal-02094581.

(Continued)

*Primary Examiner* — Amanda Lauritzen Moher
*Assistant Examiner* — Delia M. Appiah Mensah
(74) *Attorney, Agent, or Firm* — Diederiks & Whitelaw, PLC.

(57) ABSTRACT

A method of processing cardiac ultrasound data for determining information about a mechanical wave in the heart. The method comprises receiving data representative of a time series of three-dimensional data frames, generated from ultrasound signals from a human or animal heart, each frame comprising a set of voxels, each voxel value representing an acceleration component of a respective location in the heart at a common time. The method also comprises identifying, for each voxel, a frame of the series in which the voxel value is at a maximum. A three-dimensional time-propagation data set is generated by assigning each voxel a value representative of the time of the respective frame in the time series for which the corresponding voxel is at a maximum. The method then comprises generating data representative of a three-dimensional velocity vector field by calculating time derivatives from the three-dimensional time-propagation data set.

23 Claims, 11 Drawing Sheets

(51) Int. Cl.
*A61B 8/00* (2006.01)
*A61B 5/318* (2021.01)

(52) U.S. Cl.
CPC ............ *A61B 8/4488* (2013.01); *A61B 8/483* (2013.01); *A61B 8/488* (2013.01); *G06T 15/08* (2013.01); *G06T 2210/41* (2013.01)

(56) References Cited

U.S. PATENT DOCUMENTS

| | | |
|---|---|---|
| 2008/0095417 A1 | 4/2008 | Pedrizzetti et al. |
| 2015/0327838 A1* | 11/2015 | Francis ................ A61B 8/4433 600/459 |
| 2018/0220997 A1 | 8/2018 | Song et al. |
| 2018/0253854 A1 | 9/2018 | Falahatpisheh et al. |
| 2021/0145361 A1* | 5/2021 | del Alamo de Pedro ................... G16H 30/40 |

OTHER PUBLICATIONS

Salles, Sebastien, et al. "Clutter Filter Wave Imaging: A New Way to Visualize and Detect Mechanical Waves Propagation." *2017 IEEE International Ultrasonics Symposium (IUS)*, 2017, doi:10.1109/ultsym.2017.8092882.

* cited by examiner

ULTRASOUND CARDIAC PROCESSING

BACKGROUND OF THE INVENTION

This invention relates to cardiac ultrasonography, e.g. for determining information about a mechanical wave in the heart.

It has been known for many years to use ultrasound imaging techniques to image human and animal hearts, and to analyse the acquired image data in order to extract clinically useful information.

Mechanical waves are oscillations of matter, which transfer energy through a medium. Mechanical waves are generated in the human body by the motion of the heart and blood passing through it—e.g. a shear wave is generated due to the closing of the aortic valve. These mechanical waves can be detected both in the heart and in the arteries closely surrounding the heart. Exactly how they travel through the heart can depend the health of the heart. Thus, it can be desirable to analyse the motion of such waves, e.g. in order to gain insights into patient health.

It is known in the art to use ultrasound imaging to detect mechanical waves within the heart, for example as described in "Clutter Filter Wave Imaging", Salles et al., 2019, IEEE Transactions on Ultrasonics, Ferroelectrics, and Frequency Control. PP. 1-1. 10.1109/TUFFC.2019.2923710, and in "Natural mechanical wave detection using ultrafast ultrasound and velocity Clutter Filtering Wave Imaging", Salles et al., 2019, HAL Id: hal-02094581.

However, the information which is obtained using currently known ultrasound techniques can be difficult to analyse and interpret.

It is therefore desired to provide improved methods of processing and imaging cardiac mechanical waves.

SUMMARY OF THE INVENTION

From a first aspect, the invention provides a method of processing cardiac ultrasound data for determining information about a mechanical wave in the heart, comprising:
  receiving data representative of a time series of three-dimensional data frames, generated from ultrasound signals from a human or animal heart, wherein each frame comprises a set of voxels, each voxel of the frame having a value representative of an acceleration component of a respective location in the heart at a common time;
  identifying, for each voxel in the series of frames, a frame of the series in which the value of the voxel is at a maximum;
  generating a three-dimensional time-propagation data set comprising a set of voxels corresponding to the voxels of the data frames, by assigning each voxel of the data set a value representative of the time of the respective frame in the time series for which the corresponding voxel in the time series is at a maximum; and
  generating data representative of a three-dimensional velocity vector field by calculating time derivatives from the voxels of the three-dimensional time-propagation data set.

From a second aspect, the invention provides an ultrasound data-processing apparatus for determining information about a mechanical wave in the heart, comprising:
  a processing system, configured to:
    receive data representative of a time series of three-dimensional data frames, generated from ultrasound signals from a human or animal heart, wherein each frame comprises a set of voxels, each voxel of the frame having a value representative of an acceleration component of a respective location in the heart at a common time;
    identify, for each voxel in the series of frames, a frame of the series in which the value of the voxel is at a maximum;
    generate a three-dimensional time-propagation data set comprising a set of voxels corresponding to the voxels of the data frames, by assigning each voxel of the data set a value representative of the time of the respective frame in the time series for which the corresponding voxel in the time series is at a maximum; and
    generate data representative of a three-dimensional velocity vector field by calculating time derivatives from the voxels of the three-dimensional time-propagation data set.

From a third aspect, the invention provides software, or a signal or tangible medium bearing said software, comprising instructions which, when executed by a processing system, cause the processing system to:
  receive data representative of a time series of three-dimensional data frames, generated from ultrasound signals from a human or animal heart, wherein each frame comprises a set of voxels, each voxel of the frame having a value representative of an acceleration component of a respective location in the heart at a common time;
  identify, for each voxel in the series of frames, a frame of the series in which the value of the voxel is at a maximum;
  generate a three-dimensional time-propagation data set comprising a set of voxels corresponding to the voxels of the data frames, by assigning each voxel of the data set a value representative of the time of the respective frame in the time series for which the corresponding voxel in the time series is at a maximum; and
  generate data representative of a three-dimensional velocity vector field by calculating time derivatives from the voxels of the three-dimensional time-propagation data set.

Thus it will be seen that, in accordance with the invention, a 3D velocity vector field is generated for the heart based on the propagation of times of a maximum acceleration through the heart. This allows the propagation of a natural mechanical wave through the heart, in three dimensions, to be identified and potentially imaged. Information about the propagation of mechanical waves in three-dimensions, and the optional displaying of images representing this data, may provide useful clinical information about the heart to a clinician who views the image data. This development may offer an improved scientific understanding of mechanical wave behaviour in hearts in general. Moreover, it is believed that data obtained using embodiments of this approach may provide clinically useful information, such as an indication of fibre orientation of the heart, or even a new pathologic marker.

The method may comprise determining information about a mechanical wave in the heart, which may be a shear wave, a pressure wave or a pulse wave. The information may comprise the data representative of the three-dimensional velocity vector field and/or output data derived therefrom.

In some embodiments, the method further comprises generating output data from the data representative of the three-dimensional velocity vector field. The output data may be image data, e.g. for display on a display apparatus. In some embodiments, the method further comprises displaying the image data on a display apparatus, such as on a flat-panel monitor or through a stereoscopic virtual-reality headset.

In some embodiments, the output data may be exported as numerical values for further analysis, or used as input to another algorithm—e.g. an automated diagnosis system. This may be instead of or additional to generating and displaying display data.

The method may comprise generating, from the three-dimensional velocity vector field, two-dimensional output data representing (i) orientations of the three-dimensional velocity vector field; and/or (ii) magnitudes of the three-dimensional velocity vector field.

Generating the output data may comprise reconstructing one or more trajectories from the data representative of three-dimensional velocity vector field—e.g. one or more streamlines (or streamline segments). Generating the output data may comprise performing a vector field visualisation process, such as streamline simulation. Generating the output data may comprise applying an integration process to the data representative of the velocity vector field. It may comprise performing a Runge-Kutta method, e.g. a fourth-order Runge-Kutta method. The image data may represent a planar section through the heart, or may represent a projection of a three-dimensional surface. Generating the image data may comprise performing a 3D rendering step.

The time derivatives may be calculated in three dimensions—e.g. by calculating respective time derivatives along one, two or three orthogonal axes. In some embodiments a time derivative is calculated for each voxel in the time-propagation data set. A time derivative for a voxel may be calculated from a neighbourhood around the voxel—e.g. from the time values in one or more immediately adjacent voxels. Calculating the time derivative may comprise subtracting a time value of a voxel from a time value of an adjacent voxel. The time derivatives may be calculated taking account of the spatial resolutions of the data set along one or more axes. The may be helpful if the 3D data frames have different resolutions along different respective axes. The step of calculating time derivatives may be carried out by the processing system.

It has been appreciated that calculating absolute velocity vectors may not be necessary in order to extract useful information from the data. Hence, in some embodiments, rather than using the absolute distance between voxels, in each of the x, y and z directions, to differentiate each voxel, the data representative of a three-dimensional velocity vector field may be time-difference data which has not been used to divide distance information relating to the spacing between voxels. In other words, the data may be proportional to the inverse of velocity. This may preserve accuracy by avoiding a division operation which could introduce noise due to rounding errors. This differentiation thus does not produce a vector which represents the absolute velocity vector, but it still represents the direction and relative magnitude of the vectors in the vector field, and fully represents the velocities subject to knowing the voxel spacing.

It is possible to apply the technique described herein to three-dimensional data frames which have already been acquired, however some embodiments advantageously comprise a system which for acquiring the data frames. Thus, in some embodiments, the method further comprises acquiring the series of three-dimensional data frames. In some embodiments, the ultrasound imaging apparatus comprises an ultrasound probe, comprising an array of ultrasound transducers (which may be a two-dimensional array). The ultrasound probe and the processing system may be configured for acquiring the series of three-dimensional data frames.

In some embodiments, acquiring the series of three-dimensional data frames may comprise acquiring high-frame rate three-dimensional Doppler ultrasound data—e.g. of part or all of the heart.

The respective common time for each three-dimensional data frame may be a common time period. It may equal or relate to the time taken to complete one 3D Doppler scan of the heart, or of a region of the heart. The value representative of the time of a respective frame may be a time of a start or mid-point of such a time period.

In some embodiments, acquiring the series of three-dimensional data frames comprises transmitting a series of ultrasound waves towards part or all of the heart, over a time window. The ultrasound waves may be plane or diverging ultrasound waves (also known as unfocused or defocused waves). It may comprise receiving reflections of a series of ultrasound waves. It may comprise processing the received reflections to generate a time series of three-dimensional Doppler data sets, wherein each three-dimensional Doppler data set represents velocities at locations in the heart. It may comprise calculating time derivatives of velocities within a Doppler data set.

It will thus be appreciated that the data representative of the time series of three-dimensional data frames may be received from outside the apparatus (e.g. over a cable or network interface), but may be received internally within the apparatus (e.g. via an internal memory such as RAM) as part of a processing method.

References herein to the human or animal heart may encompass any part of the heart and/or blood vessels immediately adjoining the heart, such as the carotid artery.

In some embodiments, a clutter filter may be applied to each three-dimensional Doppler data set. This may advantageously attenuate or remove from the data set a range of velocity values—e.g. a range selected by a user as being of interest. This range of velocity values may be selected to encompass a velocity component of the mechanical wave (e.g. a mean or maximum expected or actual group velocity of the mechanical wave). As a result, after further processing of the data sets, regions in which these velocity values are present may be apparent by an absence of other data. In some embodiments the clutter filter may be applied by applying a high-pass filter to the three-dimensional Doppler images.

In some embodiments, a spatiotemporal filter may be applied to the time series of three-dimensional Doppler data sets. This advantageously smooths the series of images, increasing the signal-to-noise ratio of the images.

In some embodiments, envelope detection may be carried out on the three-dimensional Doppler images. This may produce a 3D brightness-mode (B-mode) image with improved image quality.

In some embodiments, the method further comprises selecting the time series of frames in which a mechanical wave propagates through the region from a longer set of three-dimensional data frames, e.g. as a time window of interest. Data frames outside the period of interest may be discarded. This advantageously allows the particular time window of interest to be selected, and any data from outside of this time window to be removed, thus significantly reducing the quantity of data which is to be processed and thereby making the imaging method both faster and more efficient. In some embodiments, a period of interest, in which a mechanical wave propagates through the region, may be determined using electrocardiography (ECG). The ultrasound imaging apparatus may comprise an electrocardiogram device, which may be configured to be used to determine a period of interest in which a mechanical wave propagates through a region of the heart. This may allow the period of interest to be detected automatically, and the irrelevant data frames to be removed automatically.

In some embodiments, the method may further comprise applying a segmentation process, e.g. to identify one or more structures within the heart. The segmentation process may use other ultrasound images of the heart, which may be intensity-based (i.e. non-Doppler). These other images may be acquired at a lower frame rate and/or higher spatial resolution than the Doppler data sets or the acceleration data frames. The method may comprise removing, from the series of three-dimensional data frames, data which corresponds to a region of the heart which does not contain a structure of interest. The method may comprise acquiring such ultrasound images of the heart. This step advantageously allows structures of interest to be identified within the images, if the Doppler images are of too low resolution to identify structures within them accurately. The additional use of images, which are of higher quality, allows structures within the images to be reliably identified. Any data which does not correspond to the structure of interest may then be removed from the high-frame rate images, thus reducing the amount of data to be processed and making the method faster and more efficient. For example, the segmentation process may allow identification of the left ventricle of a patient's heart, and thus it would be possible to only keep data relating to the left ventricle, and to discard all other data.

The values representative of acceleration in the data frames may be represented in any appropriate format. They preferably scale linearly with acceleration. They may be calibrated values—e.g. in $m/s^2$—or they may be in any other appropriate unit.

By determining the time at which each voxel experiences a maximum acceleration, within the time window, the propagation of a wavefront past the locations in the heart can be determined.

The time values in the three-dimensional time-propagation data may be represented in any appropriate format. They may be values expressed in seconds or milliseconds, or in any other appropriate unit of time.

The processing system may be configured to implement some or all steps disclosed herein. The processing system may take any suitable form. It may comprise one or more of: a central processing unit, a graphics processing unit, a microcontroller, an ASIC, an FPGA, and any other discrete or integrated components or circuitry. It may comprise memory storing software instructions for instructing a processor to perform some or all of the steps disclosed herein. The processing system may be a single processing unit or device, or it may be distributed—e.g. comprising one or more servers. Processing may be carried out on a single device or may be shared across multiple devices in any appropriate way. For instance, one device may generate data representing a velocity vector field and a different device (possibly remote from the first) may determine a streamline or streamline segment and/or display the output data. In some embodiments, sampled image data may be collected by a first device (e.g. an ultrasound scanner) and sent to a remote computer or server which applies some or all of the processing operations.

Features of any aspect or embodiment described herein may, wherever appropriate, be applied to any other aspect or embodiment described herein. Where reference is made to different embodiments or sets of embodiments, it should be understood that these are not necessarily distinct but may overlap.

BRIEF DESCRIPTION OF THE DRAWINGS

Certain preferred embodiments of the invention will now be described, by way of example only, with reference to the accompanying drawings, in which.

DETAILED DESCRIPTION

Figure 1:
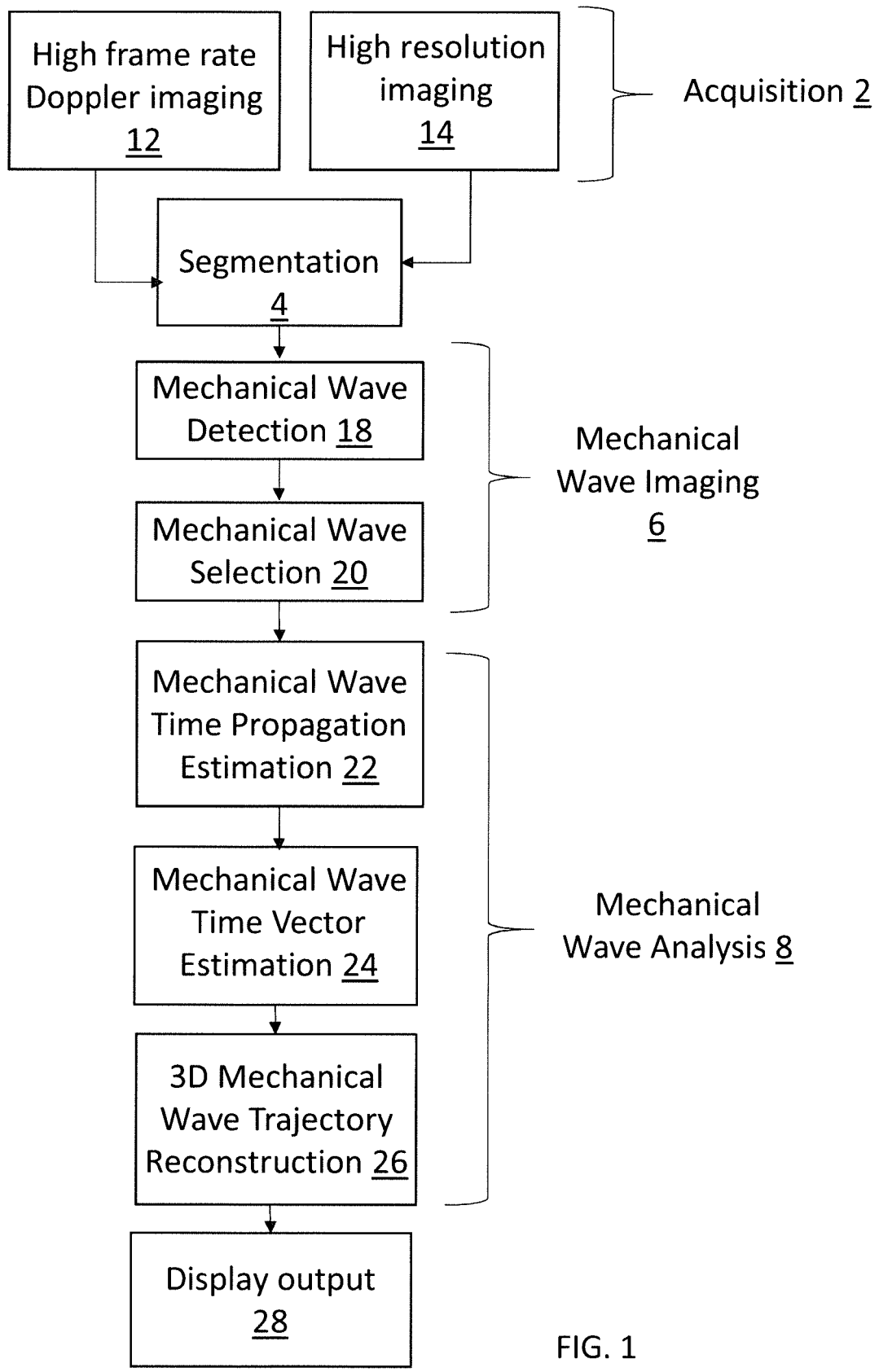
FIG. 1 is a flowchart showing the stages of a method of cardiac imaging embodying the present invention.

Throughout the figures, like reference numerals have been used for like elements.

FIG. 1 is a flowchart showing an overview of the stages of a method of cardiac imaging embodying the present invention, in which the motion of natural mechanical waves in the heart are used to help visualise the heart tissue. Each of these stages will be described in detail with reference to the later Figures.

Figure 2:
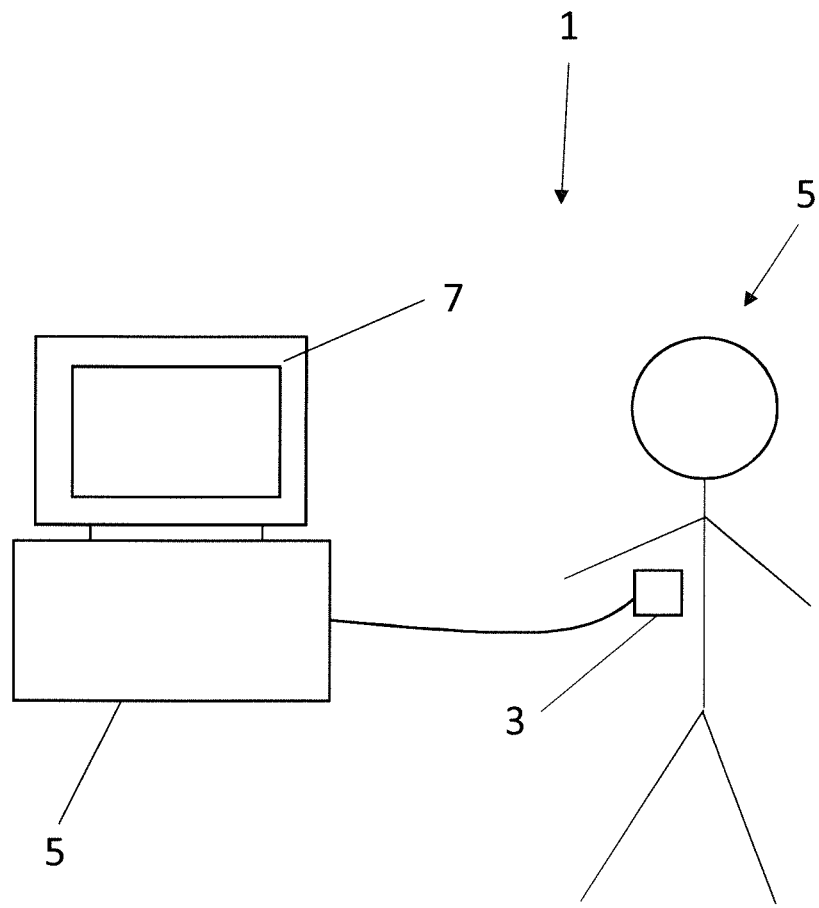
FIG. 2 is a figurative drawing showing an ultrasound system embodying the present invention.

The ultrasound imaging process is carried out by an ultrasound imaging system 1, as shown in FIG. 2. The imaging system 1 includes a handheld ultrasound probe 3, a processing unit 5, and a display 7. The ultrasound probe 3 contains an array of ultrasound transducers for transmitting signals (e.g., a series of pulses) and for receiving reflections of the signals, under the control of the processing unit 5. The array of ultrasound transducers in the ultrasound probe 3 is a two-dimensional transducer array, which can capture three-dimensional data. This probe is used to generate image data in a 3D volume. Beamforming can be used to steer the transmitted signals in a particular direction and/or to receive reflections from a particular direction.

The ultrasound imaging system 1 is used by an operator, such as sonographer or physician, to see inside the body of a patient 9. In particular, the system 1 can be used to visualise the heart and/or surrounding blood vessels.

The processing unit 5 contains a processor, memory, and other components (not shown) for controlling the transmission of signals from the probe 3, and for processing the received signals. The processing unit 5 may be conventional, apart from the software that it executes in order to implement features embodying the present invention. However, it may have non-standard hardware in some embodiments. The processing unit 5 can comprise any one of more of: a central processing unit, a graphics processing unit, a microcontroller, an ASIC and an FPGA. It may execute software instructions stored in a memory. In some embodiments, a remote server (not shown) may be connected to the processing unit 5 by a network and may be used to perform at least some of the described processing operations.

The first stage of the imaging process is an acquisition stage 2, during which a high frame rate imaging is performed, in addition to a conventional lower-frame-rate but higher-resolution imaging. These two types of ultrasound imaging are carried out in close succession, or interleaved in time.

The method begins with the acquisition, at high frame rate, of 3D Doppler ultrasound images of a region, shown in FIG. 1 as the stage "high frame rate imaging" 12. In order to produce a single 3D Doppler image, a series of plane ultrasound waves are transmitted from the probe 3 towards the patient's heart. The probe 3 receives the reflections of these signals, and the probe 3 or the processing unit 5 processes the received signals to generate a three-dimensional data set. The reflected signals received for each voxel of the three-dimensional data set are phase-shifted compared to the transmitted signals, and, as is well known in Doppler techniques, the observed phase shift is used to calculate, for each voxel, the velocity at which the corresponding point in the imaged region is moving towards the ultrasound transducer.

A single "burst" of ultrasound signals is thus processed to form a single 3D volumetric frame. This imaging process is then repeated rapidly (i.e. at a high frame rate), so that a time-series of such 3D frames are acquired, for a desired region of the heart. In some examples, the 3D ultrasound velocity frames are generated at a rate of 820 frames per second.

The second ultrasound imaging process used in the acquisition stage 2 is conventional 3D ultrasound imaging 14. This stage uses intensity-based, rather than Doppler, ultrasound imaging, as is known in the art, to obtain ultrasound 3D images of the volume of the region to be imaged, at a lower frame rate, for example approximately 15 frames per second. These ultrasound images are of much higher resolution than the images obtained from high frame rate imaging 12.

The higher resolution of the conventional ultrasound images allows structures of interest to be identified in these images, using a segmentation process or algorithm, applied by the processing unit 5. For example, a heart, or a particular structure of the heart (e.g. the left ventricle) may be clearly visible in the conventional ultrasound images, but not identifiable at all in the high frame rate Doppler ultrasound images. Once the structure of interest has been identified, the processing unit 5 removes the other, irrelevant data from the Doppler image frames. This therefore reduces the amount of data which has to be processed at later stages of the method.

The next stage of the cardiac imaging process is shown in the flowchart as mechanical wave imaging 6, and comprises two steps—first, mechanical wave detection 18, followed by mechanical wave selection 20. The first step 18 is to detect mechanical waves within the high-frame rate Doppler images. This stage is shown in more detail in FIG. 3.

Figure 3:
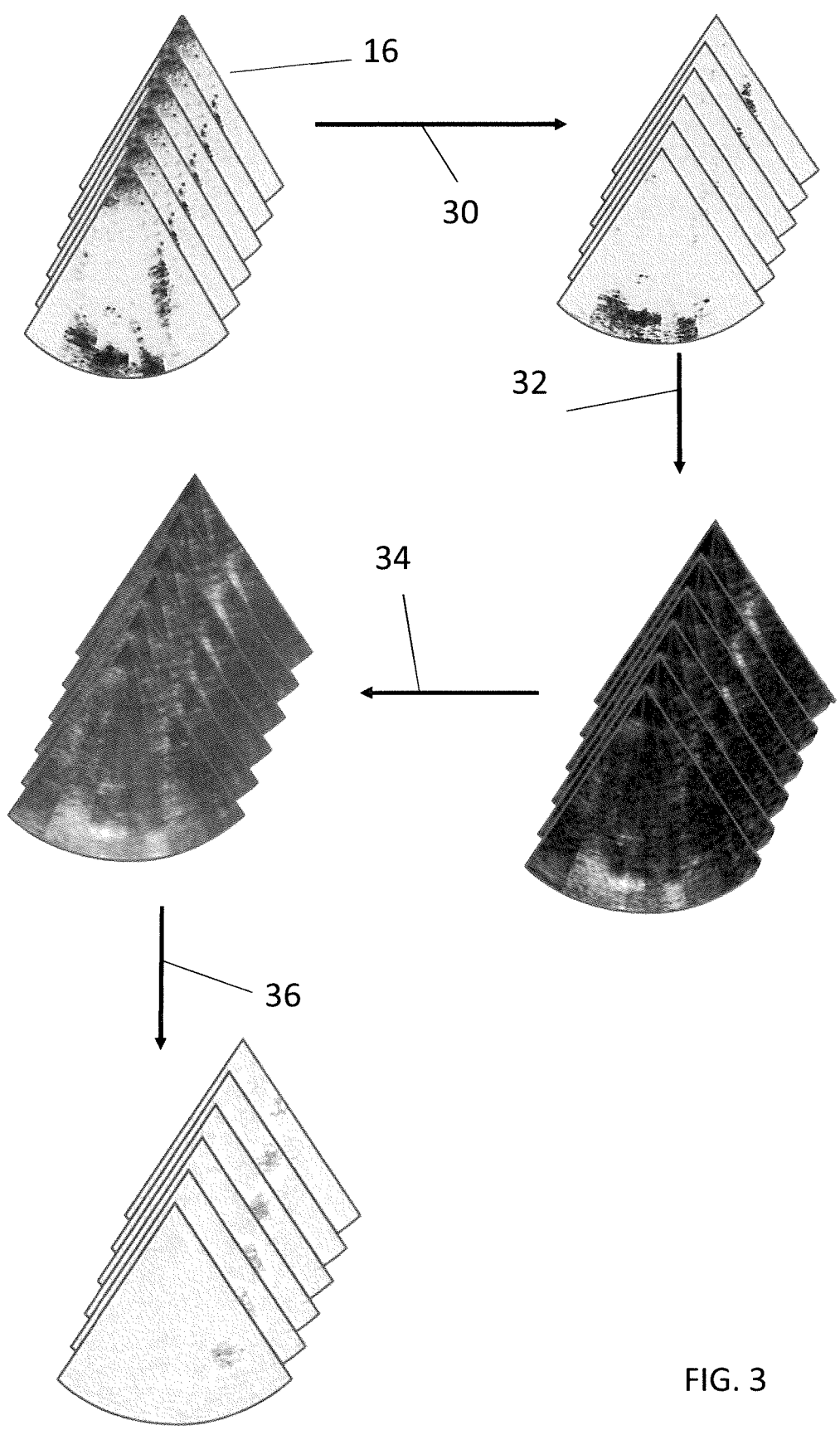
FIG. 3 is a flowchart representing the stages of a mechanical wave detection process of the method of cardiac imaging.

The mechanical wave detection stage 18 begins by applying a clutter filter 30 to the time-series of high frame rate 3D Doppler images 16 obtained from high frame rate imaging carried out at stage 12, excluding the data which was identified as irrelevant at the segmentation stage 4. An example of a series of ultrasound images, undergoing the mechanical wave detection stages, is shown in FIG. 3 for illustrative purposes. The ultrasound images shown in FIG. 3 are, for illustrative purposes, represented as a series (in time) of two-dimensional images; however, in reality, the clutter filter is applied to a series of three-dimensional images. (The term "image" is used herein to refer to any pixel- or voxel-based data set, which may include intensity and/or phase data; it is not limited to data in a form suitable for direct rendering.)

The ultrasound imaging clutter filtering, or Clutter Rejection Filtering (CFR), is here used to reject or attenuate only a range of tissue velocity corresponding to velocities induced by the mechanical waves in the heart. Such velocities are thus rejected or attenuated. Thus, the propagation of this range of tissue velocity will be represented as a darker grey band in the brightness-mode data sets—i.e. by an absence of data. This principle is depicted in FIG. 4.

Figure 4:
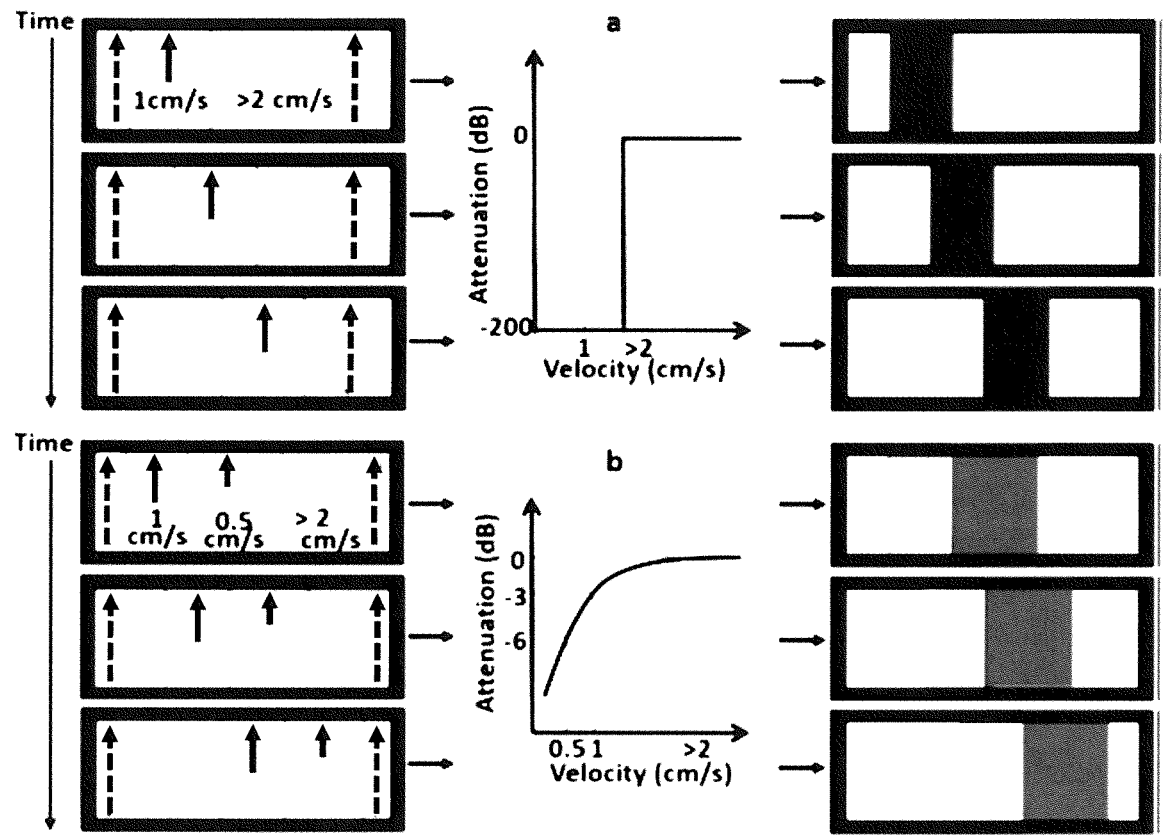
FIG. 4 is a set of schematic images and graphs, demonstrating the principle of clutter filtering.

Graph a of FIG. 4 shows a medium moving with two axial velocities (1 cm/s—solid arrow, and >2 cm/s—dashed arrow). These velocities are filtered with an ideal high pass filter with a cut-off velocity at 2 cm/s (as shown), and the resulting brightness-mode (B-mode) images of the medium are shown on the right hand side. The resulting images contain a fully attenuated (black) region, which corresponds to the removed 1 cm/s velocity. FIG. 4 also shows a different example in graph b, in which a medium is moving with three axial velocities (1 cm/s and 0.5 cm/s with solid arrows, and >2 cm/s with a dashed arrow) which are filtered with a conventional high pass filter with a cut-off velocity>2 cm/s. The resulting B-mode images of the medium, shown on the right of graph b, contain partially attenuated (grey) regions corresponding to the attenuated 1 cm/s and 0.5 cm/s velocities. As those velocities propagate through the medium, the grey regions also propagate.

Figure 5:
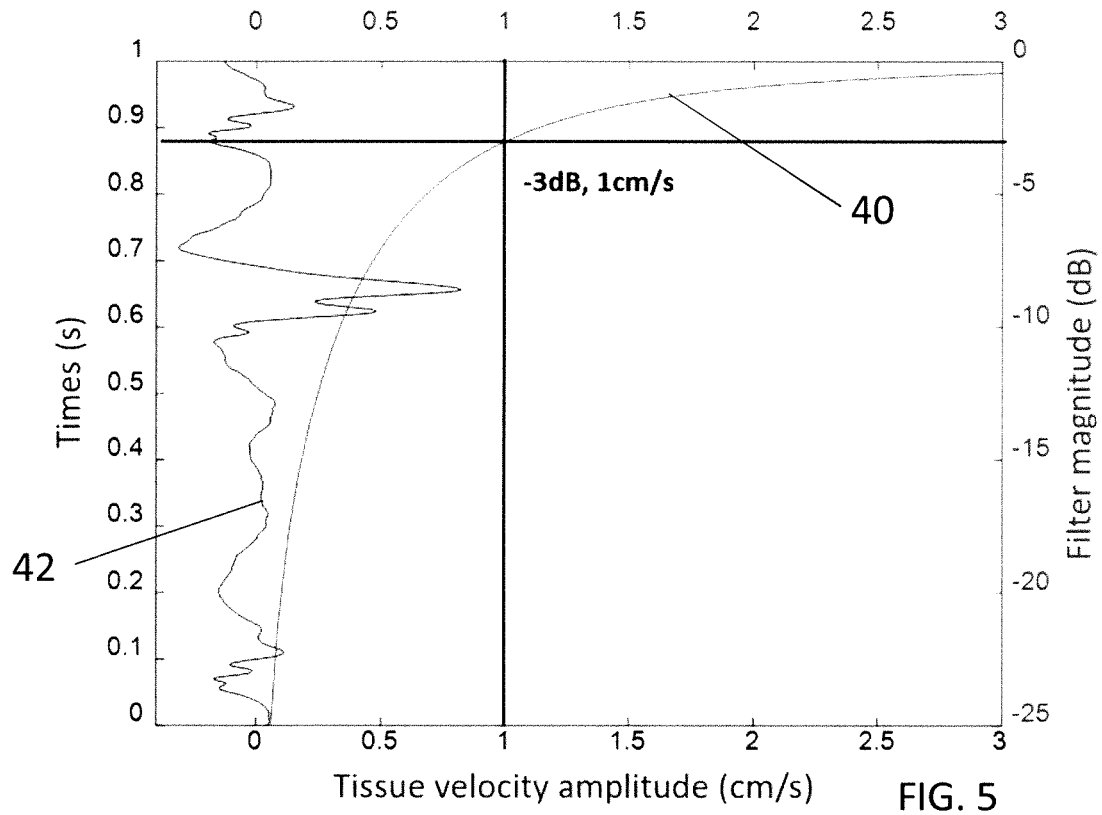
FIG. 5 is a graph representing a tissue velocity signal, and a high pass filter applied to such a signal, during clutter filtering.

In the present embodiment, the clutter filtering principle is applied so that the Doppler frequencies of the ultrasound image volumes are attenuated to select a particular bandwidth of wave propagation velocities which are of interest, specifically the expected velocities of the mechanical waves propagating in the imaged region of the heart. Several filter designs could be used. In this example, a causal first-order high-pass Butterworth filter was used. The filter was applied in the time dimension. The normalized cut-off frequency $f_{C_n}$ is defined as $$f_{C_n} = \frac{V_C}{vNyq}$$

with $$vNyq = \frac{c_0 x\ FPS}{4f_0}$$

and $$f_c = fc_n x\ FPS/2$$

where Vc is the cut-off velocity, to be chosen according to the tissue velocity of the studied medium, $c_0$ is the speed of sound, FPS is the frame rate, $f_0$ the transmit frequency, vNyq the Nyquist velocity, and $f_c$ the cut-off frequency in Hz FIG. 5 shows an example of a high-pass filter used for clutter filtering in some embodiments. Line 40 shows the filter magnitude (shown on the right hand axis, in units of decibels, dB) against tissue velocity amplitude (x-axis, cm/s). Line 42 shows the variation of the tissue velocity amplitude of a carotid wall against time (y-axis, seconds). In this example, the cut-off frequency of a first order Butterworth filter was set at 68 Hz in order to attenuate the velocity under 1 cm/s.

Next, with reference to FIG. 3, each clutter filtered image in the time series is processed 32 to detect an envelope or B-mode image. In this example, the RF (radio frequency) high-frequency ultrasound sequences are envelope-detected using the absolute value of the Hilbert transform. The Hilbert transform imparts a phase shift of 90° to the signal, shifting the peaks in the RF data towards the troughs. The signal that is output by the Hilbert transform is then combined with the original RF signal, and the result is then envelope detected. Also in this stage, IQ (in-phase and quadrature) sequences are envelope detected using the absolute value of the IQ data. This IQ, or quadrature detection, step multiplies an in-phase sinusoid and a quadrature-phase sinusoid with the input signal, accentuating signal content of a particular frequency. The resulting signal is then envelope detected. A logarithmic compression can be performed to extract the B-mode image. The stage results in a time series of 3D images which are smoothed and in which the image data is more clearly visible—i.e. having better contrast in the images.

A spatiotemporal filter is then applied 34. Spatiotemporal averaging (low-pass filtering) of the resulting sequences can be used to increase the Signal to Noise Ratio (SNR) of the data, reducing the variance in the mechanical wave slope estimation.

A time differentiation process is then applied 36. In this process, the time sequence of 3D Doppler ultrasound images resulting from the spatiotemporal filtering 34 is differentiated in time to recover an image of the tissue acceleration. Because each 3D image represents the axial component of velocity of the points of the imaged region, at a particular instant in time, differentiating 36 this series of images gives a series of images representing the axial acceleration of each point in the region, at an instant in time.

The resulting acceleration image series is useful because the propagation of a mechanical wave through the heart can be more easily detected in an image set that shows the acceleration within a region, rather than the velocity. This is because at the "foot" of a mechanical wave, i.e. the inflection point of the mechanical wave, the acceleration (of, for example, the wall of the heart) reaches its maximum. Thus the time at which the acceleration at a particular region reaches its maximum is the point at which the mechanical wavefront passes that particular point. It is only later on in the mechanical wave cycle that a particular point will reach its peak velocity, hence why the propagation of a mechanical wavefront is not seen so clearly in a series of images showing velocity.

After the mechanical waves detection 18, using the process described above, the result is a time series of 3D images, representing the acceleration at each point in a volume of the imaging region (the volume selected during the segmentation stage 4). The next stage is mechanical wave selection 20, in which a particular time window is selected, from the total period over which ultrasound imaging was carried out—e.g. from one heartbeat. The selected time window, which is a sub-period of the total imaging period, is selected to be the time window in which a mechanical wave of interest is passing through the imaged volume. This process is represented in FIG. 6.

Figure 6:
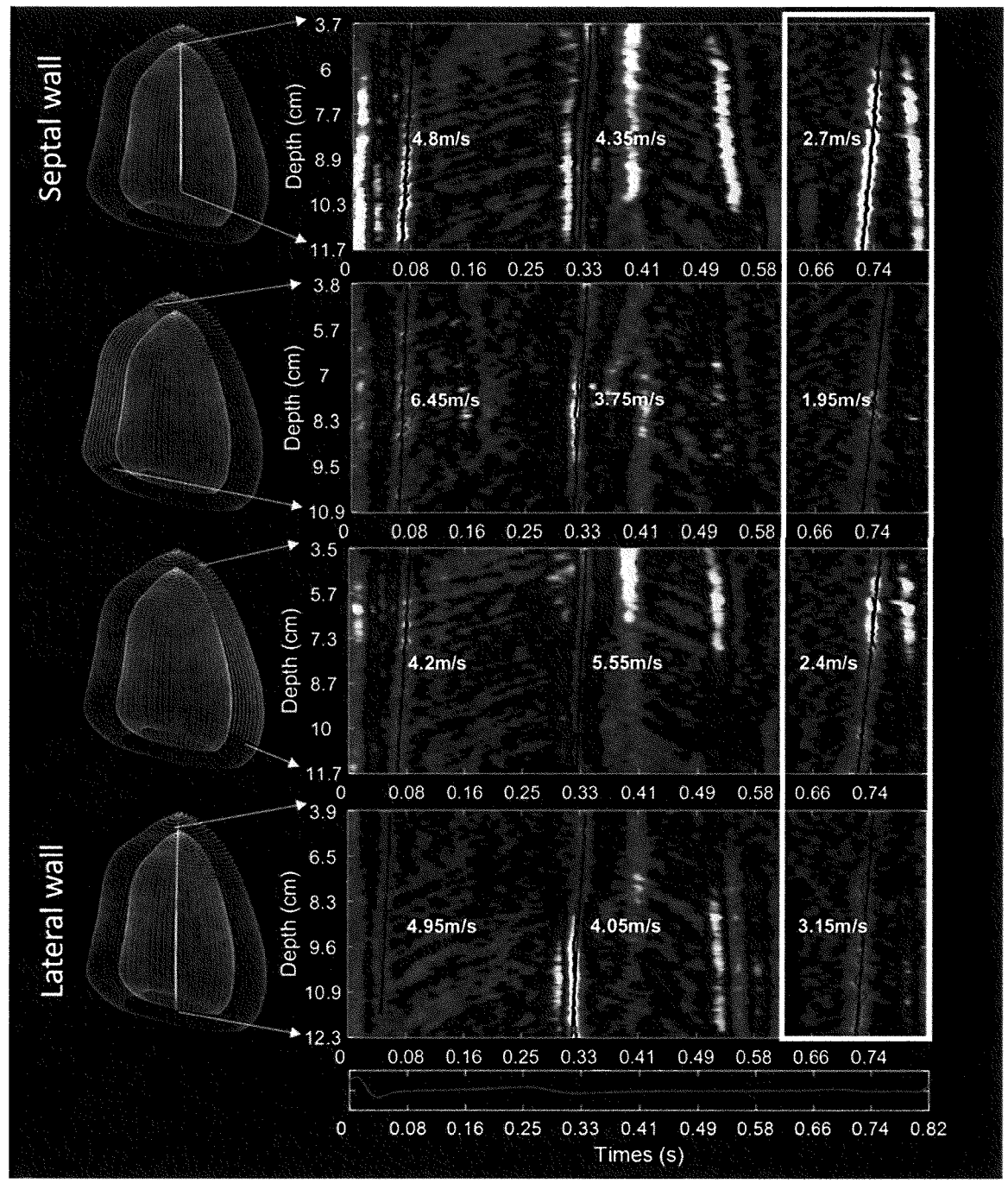
FIG. 6 is a series of time-aligned screenshots of Doppler velocity values at a range of depths, over one cardiac cycle, at each of four different locations within a patient's heart.

FIG. 6 shows four images. Each of these images represents the speeds of points along a line in an imaged region (based on the Doppler shift of the received ultrasound signal) from various depths in an imaged region (y-axis), over time (x-axis). Each of the four images shows the received signals along a respective line from four different regions of a heart. The images on the left side of FIG. 6 indicate which region each image corresponds to—for example, the top image is of data taken from the septal wall of the heart.

The total time interval across which imaging is carried out is shown along the x-axis on each of the four images. The total time period is also shown on the line graph underneath the images, which represents an electrocardiography (ECG) signal amplitude over time, i.e. a graph showing the voltage over time of electrical activity in the heart. One cardiac heart is visible on this graph.

The white rectangle spanning the four plots in FIG. 6 indicates the time region from about 0.6 s, to about 0.82 s. This represents the selection of a sub-period of interest from the total imaging period. A time period of interest could be selected (i.e. the choice of position of the white rectangle) manually, or the period of interest could be determined by correlating the image data with ECG data. ECG data could be used to identify the heart beat cycle of the imaged heart, in a manner that is known in the art. It is furthermore known in the art that there is a certain time periods, within a cardiac cycle, at which certain mechanical waves propagate through various locations within the heart. Thus for a particular imaged region, the time period of interest could be selected based on the predicted passing time of a mechanical wave, as calculated from an ECG. The selection of this sub-period of the total imaging period selects from the total filtered time series of 3D volumes a sub-set of volumes (e.g. approximately 100 volumes for the example selection rectangle shown in FIG. 6) in which the propagation of a mechanical wave of interest is seen.

Another possibility for detecting the time period of interest is based on the speed of propagation of a mechanical wave. The velocity of a mechanical wave, in a given direction (i.e. in the depth dimension) is determined by the automated or manual calculating of the gradient of pixels exceeding a threshold brightness in the four plots, corresponding to the various angled white lines in FIG. 6. The speed of a mechanical wave travelling along a respective imaging line of the plots can be calculated by calculating the gradient of the line which is identified as the mechanical wave (i.e. dividing the depth dimension of the imaging volume by the time for which the mechanical wave is propagating in that particular location of the imaging volume). Some example speeds calculated in this way are shown overlaid on the images of FIG. 6. It is possibly to estimate, with reasonable accuracy, the speed of a mechanical wave which may be of interest. Thus, by calculating the speeds of various different mechanical waves it is possible to automatically select the time-window of interest, based on it being the time window in which a mechanical wave travelling with a chosen speed, is present, within one heartbeat.

Mechanical wave analysis 8 is then carried out on the selected sub-set of volumes in the time window of interest, capturing the passage of a mechanical wave of interest.

Figure 7:
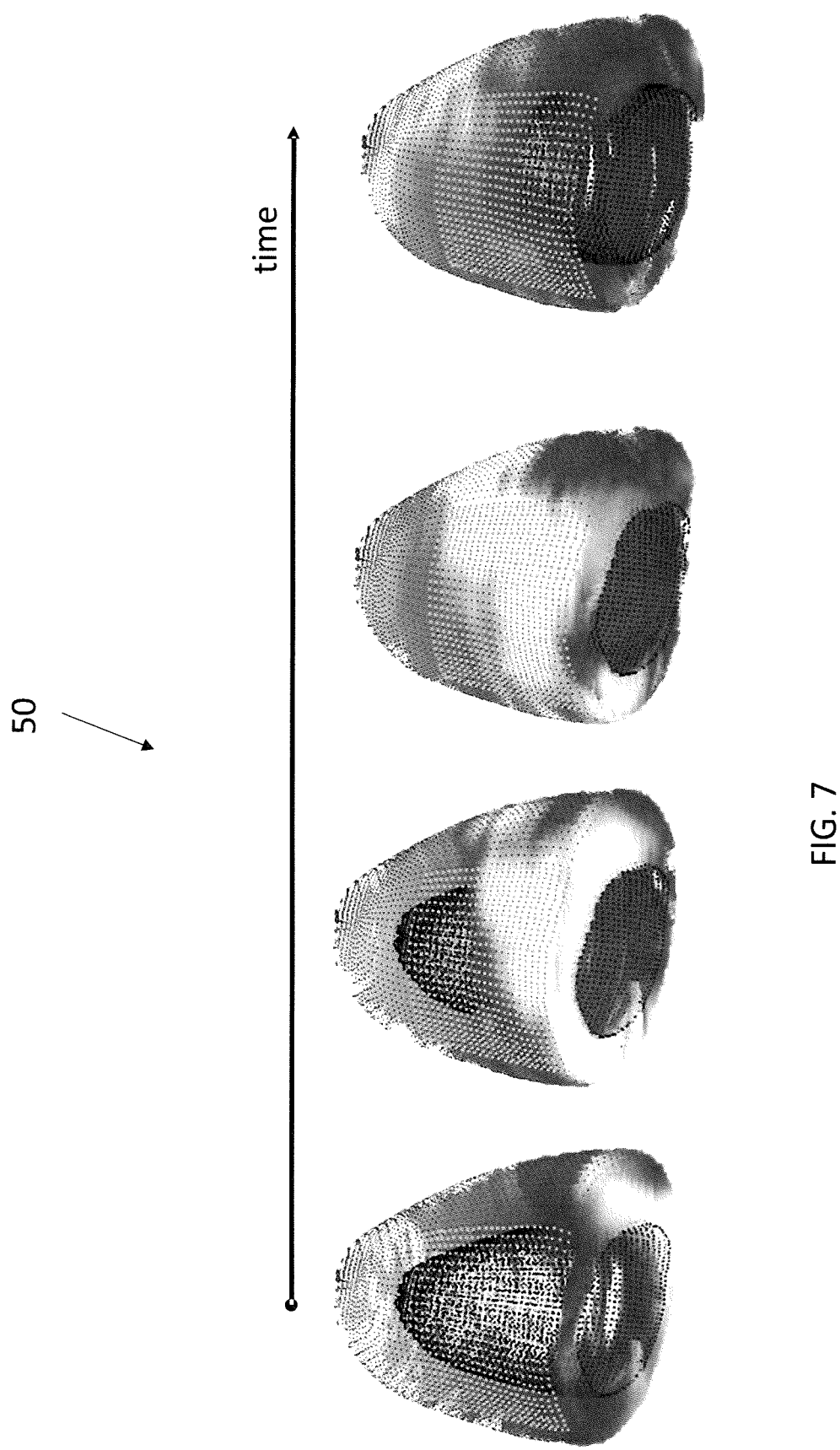
FIG. 7 is a set of four representative volumes, over time, selected from a set of approximately 100 volumes, generated by a mechanical wave selection step of the method.

The first stage of analysing the detected mechanical wave is to carry out mechanical wave time propagation estimation 22 on the selected volumes 50. The selected volumes are shown as four representative volumes in FIG. 7, although actually, in this example, there are approximately 100 volumes, each representing accelerations within the imaged region of interest, at successive instants of time. At this stage, the processing unit 5 is arranged to determine, for each voxel, the respective volume frame, of the selected sub-set of frames, in which that voxel has the maximum acceleration value.

The processing unit 5 is then arranged to generate a 3D time propagation map, being a volumetric image in which each voxel is assigned the time value of the corresponding volume frame in which it attained the maximum acceleration—i.e. the voxel value is the time, out of the selected sub-period of time, at which the maximum acceleration occurs. As discussed above, this time at which the maximum acceleration of the voxel occurs corresponds to the time at which the mechanical wave reaches that particular point, and thus the 3D volume which results from this process represents the time, from the start of the sub-period, at which the mechanical wavefront reaches each voxel within the volume.

Figure 8:
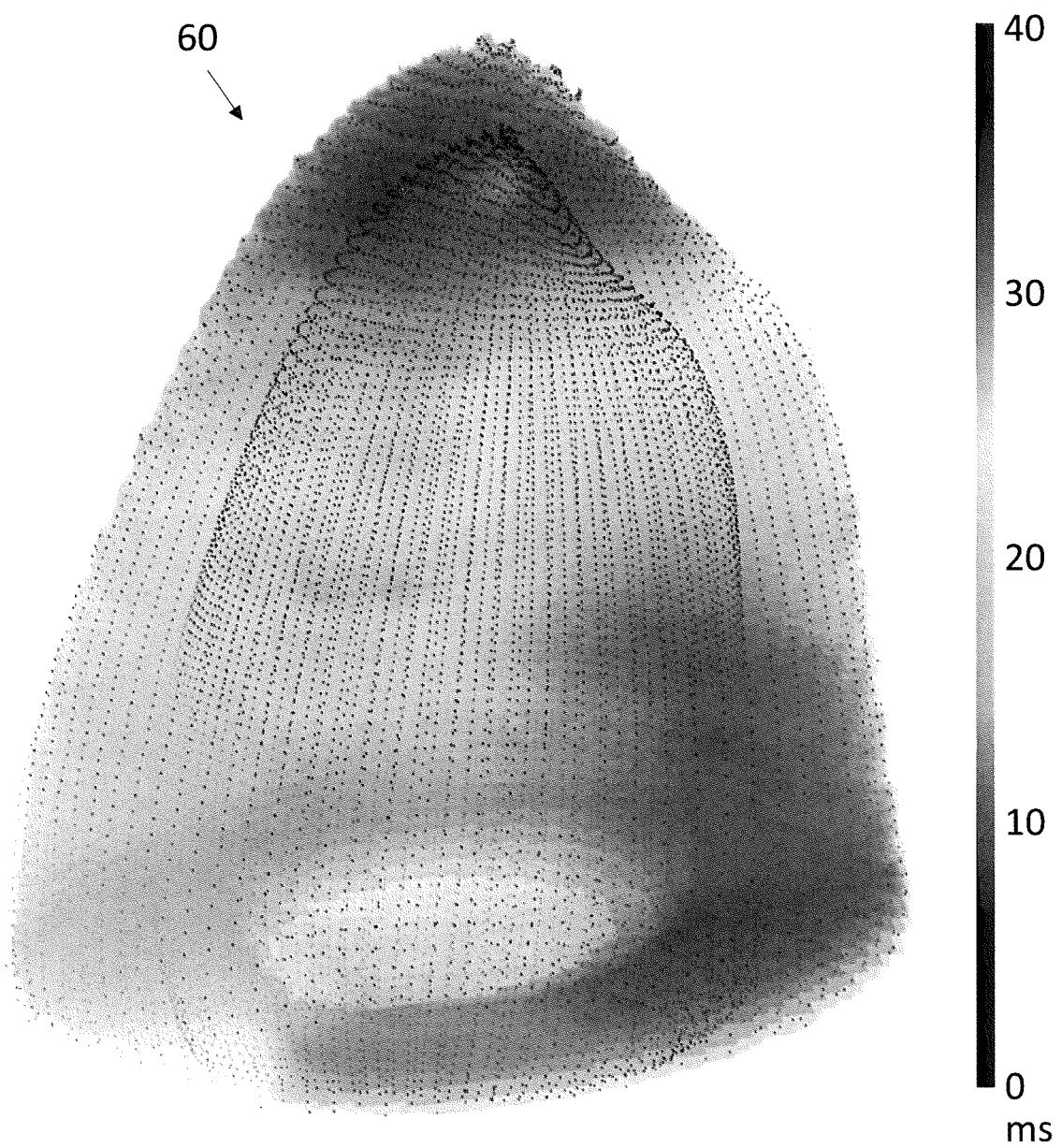
FIG. 8 is a 2D representation of the 3D time propagation map which is generated in a mechanical wave time propagation estimation stage of the imaging method.

An example of such a 3D time propagation map 60 is shown in FIG. 8. Because of the limitation of the greyscale representation, a time scale on the right hand side has been scaled so that it corresponds approximately to the shading at the same vertical height up the page. The wavefront can be seen to start in the bottom right hand corner, and spreads upwards and leftwards across the volume.

Next, a mechanical wave time vector estimation 24 is performed, in which the mechanical wave time vectors are estimated using the resulting 3D time propagation map. This is done by calculating the 3D gradient of the 3D time propagation map 60, e.g. as shown in FIG. 8, using the formula:

$$\vec{V}(x, y, z) = \left(\frac{Res_x}{dTime_x}\right) \cdot \vec{x} + \left(\frac{Res_y}{dTime_y}\right) \cdot \vec{y} + \left(\frac{Res_z}{dTime_z}\right) \cdot \vec{z}$$

where $Res_x$ is the (constant) x-axis resolution of the frame, $Res_y$ is the (constant) y-axis resolution of the frame, and $Res_y$ is the (constant) y-axis resolution of the frame. These values represent the resolution of the image in each of these three directions, and are relative values i.e. relative to each other.

The purpose of this stage 24 is to compare, for each voxel, the time at which the mechanical wave reached that particular voxel, to the time at which it reached each adjacent voxel (in the x, y and z direction). Knowing the size of each voxel would allow a distance to be assigned to the travel of the mechanical wave from a given voxel to the adjacent voxel in each direction. Thus, by dividing the distance travelled (e.g. the size of a voxel) by the difference in the time values of the two adjacent voxels, the velocity of the mechanical wave in that direction can be calculated. Calculating the velocity in all three directions allows a 3D velocity vector to be assigned to each voxel.

The 3D volume generated from the ultrasound images may, in some cases, have a different resolution in each of the x, y and z directions. For instance, a single voxel in the z-direction might correspond to a distance in the patient's heart that is twice the distance represented by a voxel in the x-direction. This could lead to incorrect vectors being calculated if the resolution were disregarded, since the velocity magnitudes in different directions would be on different scales, and thus, if combined, they would give inaccurate vectors. Thus, the formula above is used to assign a velocity vector to each voxel, taking account of the resolution of the data set in each respective direction.

Figure 9:
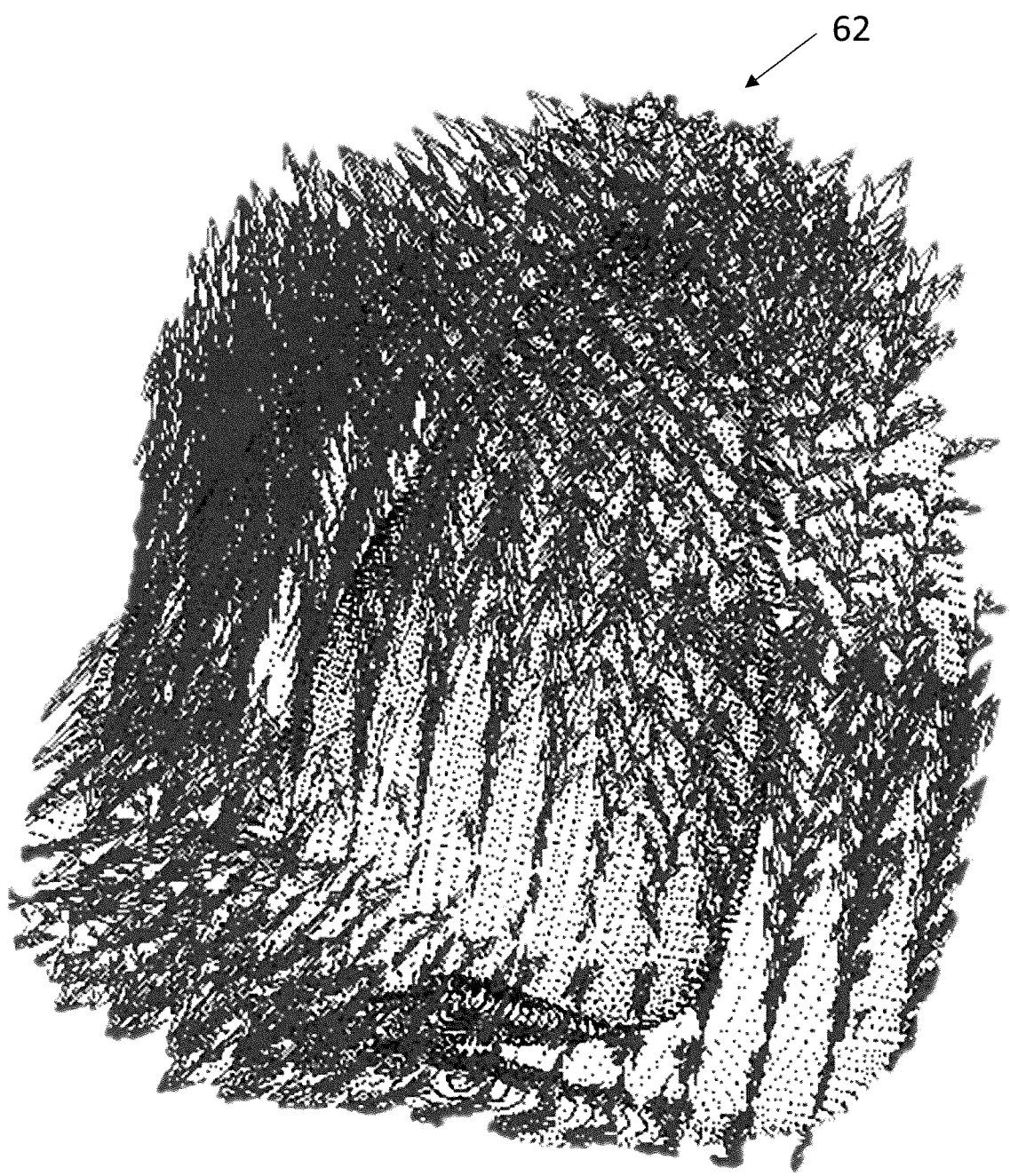
FIG. 9 is a 2D representation of the time vector field which is generated at a mechanical wave time vector estimation stage of the method.

FIG. 9 shows an example of a resulting velocity vector field 62, showing the effect of one mechanical wave. This represents a 3D spatial map of the velocity vectors arising due to the passage of the wave, at each point in the volume, across the selected time window. It does not correspond to a particular instant in time.

It has been appreciated that it is not always necessary to divide by distance (or resolution) in order to calculate an absolute velocity vector for each voxel, but rather it may be sufficient, in some embodiments, to generate a "time" vector, based on time differences, but without dividing by distance. These time vectors can represent the direction of the velocity at each voxel and the relative magnitude of their velocity vectors. By cutting out the division step, the processing load can be lessened and greater accuracy may be achieved by removing a source of noise.

A 3D mechanical wave trajectory reconstruction 26 is then performed, to process the information represented by the 3D velocity vector field (or 3D time vector field) ahead of displaying 28 it on the display screen 7.

First, the velocities arising from the detected mechanical waves, as captured by the velocity vector field 62, are used to calculate 3D trajectory lines, or streamlines. This can be done through known processes of particle tracing, using numerical integration. The streamlines show the direction in which a massless fluid element will travel at any point in time.

Any suitable technique may be used to carry out this stage, such as a first-order Euler method. However, this method is not particularly accurate. Instead, a $4^{th}$ order Runge-Kutta method has been found to give useful results, and is used in this example embodiment. The position chosen to seed the particles from in the streamline method could be chosen manually or could be determined automatically as part of a streamlining algorithm. Typically the position chosen to seed the particles from in the streamline method is either a random placement or on a grid. The streamlines may be rendered for two-dimensional display 28 on a flat screen monitor 7.

If the streamlines were not calculated, the direction of the mechanical waves could be displayed directly from the velocity vector field 62 by converting the vector directions into colour coded volumes. However, calculating streamlines allows the trajectory of the mechanical waves to be clearly visible to a user. This is particularly useful since it has been appreciated that the trajectory of a mechanical wave in the heart may be related to the cardiac fibre of the heart (e.g. the fibre orientation).

A streamline representation is one of many ways to visualise a stationary vector field. More generally, it would be understood that pathlines are used to visualise non-stationary vector fields (i.e. a vector field which is changing with time) and could be generated in some embodiments. In embodiments of the present invention, the processing is typically done on data which corresponds to a very short time period, such that the vector field may be treated as being approximately stationary, allowing streamline methods to be used. It will be understood that the streamlines are used to show the (integrated) path a massless particle would travel for the given vector field/calibration.

The streamlined output image may be processed before display (e.g., by log compression and dynamic-range adjustments) and shown on the display 7 of the ultrasound imaging apparatus 1.

Figure 10:
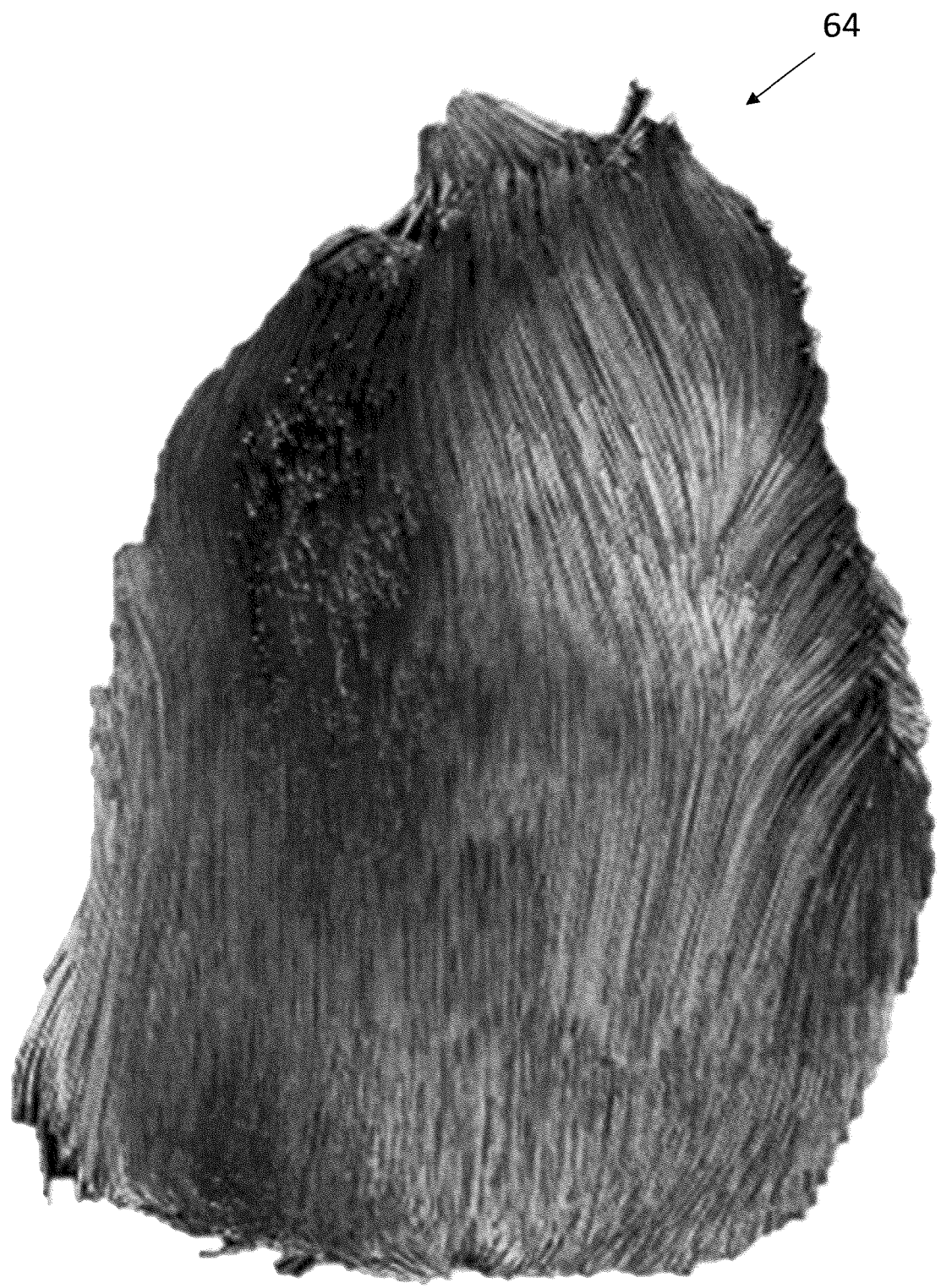
FIG. 10 is a 2D rendered image of data generated by a 3D mechanical wave trajectory reconstruction step of the method.

FIG. 10 shows a result of applying a $4^{th}$-order Runge-Kutta streamline process to the vector field represented in FIG. 9. It is a screenshot of an example output that could be shown to a clinician on the display 7. Although shown herein greyscale, in the original, colour is used to represent different directions, in order to give further visual assistance to a human viewer in interpreting the image.

Through the method as laid out above, these embodiments provide the capability to represent visually the propagation of natural mechanical waves through the heart and adjoining arteries in a way that can be readily interpreted by a human operator. This may enable clinicians to gain a better understanding of mechanical wave behaviour, which may lead to possible new pathologic markers, and may provide a global indicator of the fibre orientation of the heart (by assuming that the mechanical waves follow the tissue fibre), based on the propagation of mechanical waves.

Figure 11:
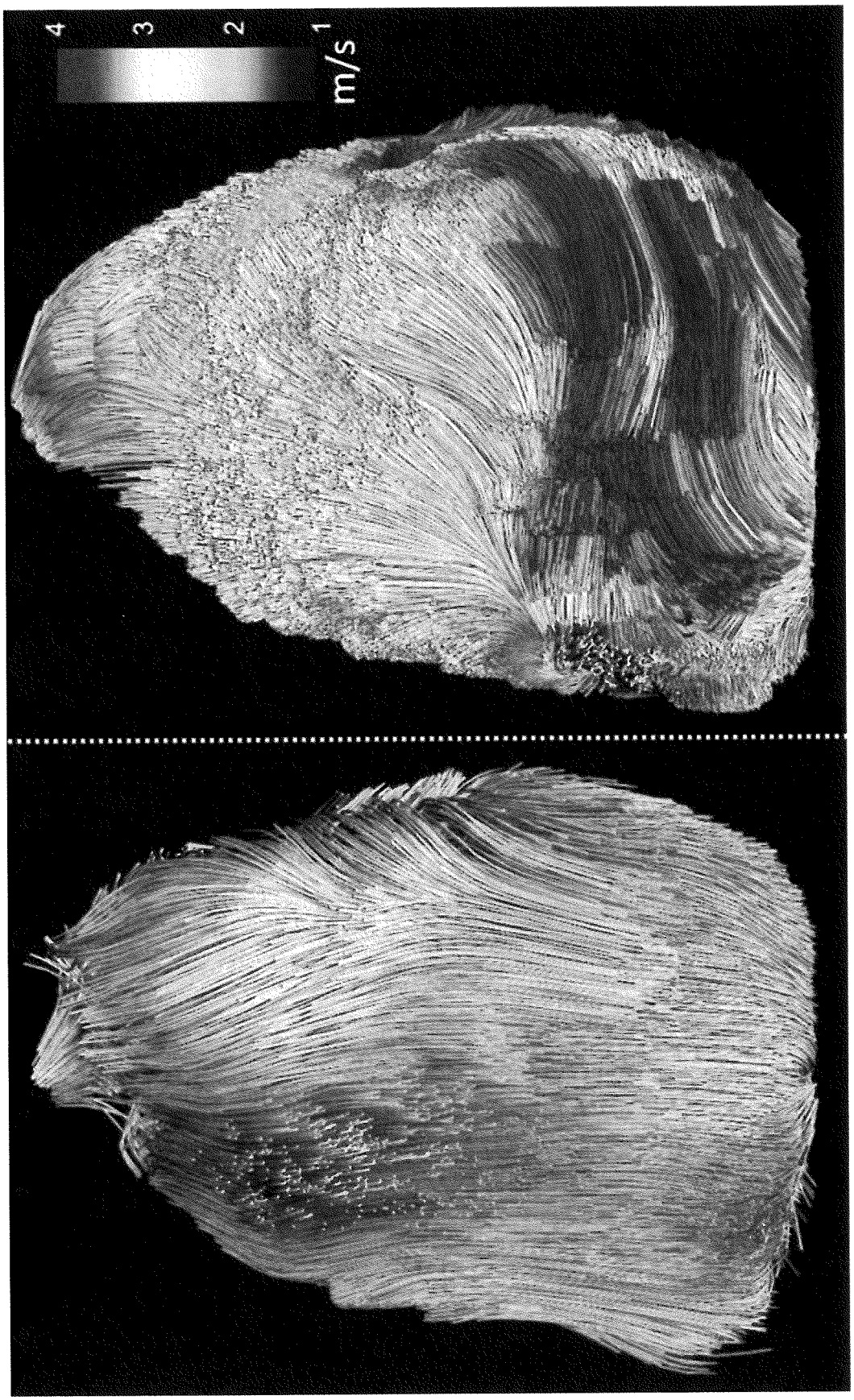
FIG. 11 is a screenshot showing the mechanical wave velocities detected in the heart of a healthy subject (left) and the heart of a patient with fibrotic tissue (right), generated using apparatus embodying the invention.
Figure 12:
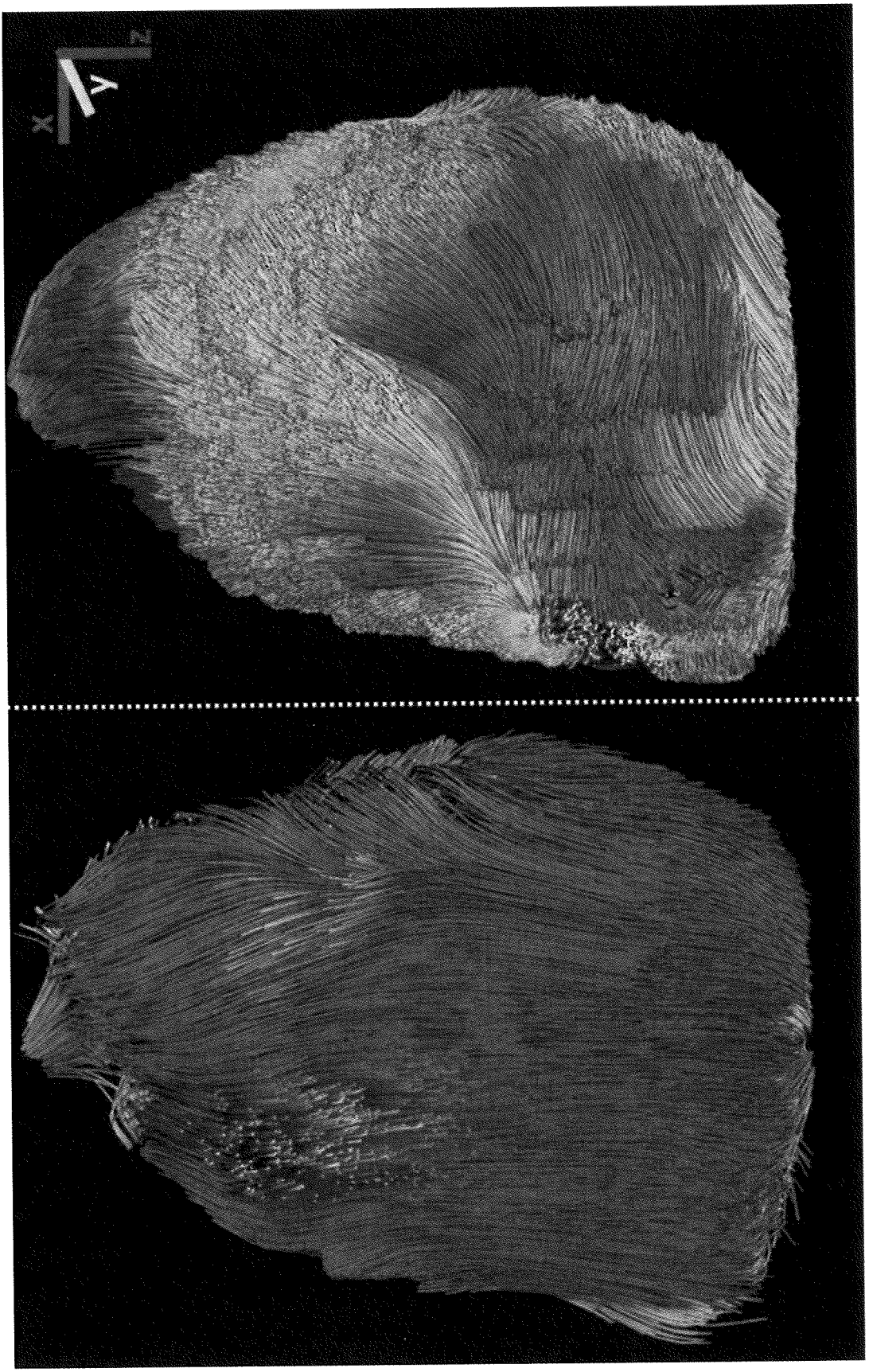
FIG. 12 is a screenshot showing the mechanical wave trajectories detected in the heart of a healthy subject (left) and the heart of a patient with fibrotic tissue (right), generated using apparatus embodying the invention.

As an example, FIGS. 11 and 12 show images of the left ventricle of the heart of one healthy subject (left) and of one patient with fibrotic tissue (right). This comparison shows differences between the two subjects in term of mechanical wave velocities (as shown in FIG. 11) and mechanical wave trajectories (as shown in FIG. 12). It is apparent from these images that 3D imaging of mechanical waves in the heart offers the possibility of improved cardiac imaging, including improved imaging of fibres within the heart.

It will be appreciated by those skilled in the art that the invention has been illustrated by describing one or more specific embodiments thereof, but is not limited to these embodiments; many variations and modifications are possible, within the scope of the accompanying claims.

The invention claimed is:

1. A method of processing cardiac ultrasound data for determining information about a mechanical wave in heart tissue, comprising:
receiving data representative of a time series of three-dimensional data frames, generated from ultrasound signals from a human or animal heart, wherein each frame comprises a set of voxels, each voxel of the frame having an acceleration value representative of an acceleration component of a respective location in the heart tissue at a common time;
identifying, for each voxel in the series of frames, a frame of the series in which the acceleration value of the voxel is at a maximum;
generating a three-dimensional data set comprising a set of voxels corresponding to the voxels of the data frames, by assigning each voxel of the data set a time value representative of the time of the respective frame in the time series for which the acceleration value of the corresponding voxel in the time series is at a maximum; and
generating data representative of three-dimensional velocity vectors, which together provide a three-dimensional velocity vector field for the mechanical wave through the heart tissue, by calculating time derivatives along three orthogonal axes, wherein each respective three-dimensional velocity vector is determined from differences between the time value assigned to a respective voxel of the three-dimensional data set and time values assigned to voxels in a neighbourhood around the respective voxel.

2. The method of claim 1, further comprising determining information about a mechanical wave in the heart tissue, wherein the mechanical wave is a shear wave, a pressure wave or a pulse wave.

3. The method of claim 1, further comprising generating, from the three-dimensional velocity vector field, two-dimensional output data representing orientations of the three-dimensional velocity vector field and/or magnitudes of the three-dimensional velocity vector field.

4. The method of claim 1, further comprising generating output data from the data representative of the three-dimensional velocity vector field, wherein generating the output data comprises reconstructing one or more trajectories from the data representative of three-dimensional velocity vector field and/or performing a vector field visualisation process.

5. The method of claim 1, further comprising:
generating image data from the data representative of the three-dimensional velocity vector field; and
displaying the image data on a display apparatus.

6. The method of claim 1, further comprising calculating a time derivative for every voxel in the data set.

7. The method of claim 1, further comprising acquiring the data representative of the time series of three-dimensional data frames by:
receiving ultrasound signals reflected from the heart tissue;
generating a time series of three-dimensional Doppler data sets from the reflected ultrasound signals, wherein each three-dimensional Doppler data set represents velocities at locations in the heart tissue; and
calculating the time derivatives of velocities within each three-dimensional Doppler data set.

8. The method of claim 7, further comprising applying a clutter filter to each three-dimensional Doppler data set, wherein the clutter filter attenuates velocity values over a range of values that contains a velocity component of the mechanical wave.

9. The method of claim 1, further comprising using ultrasound images of the human or animal heart, acquired at a lower frame rate and/or higher spatial resolution than the time series of three-dimensional data frames, to perform a segmentation process.

10. The method of claim 1, further comprising using electrocardiography (ECG) to select the time series of three-dimensional data frames from a longer series of three-dimensional data frames.

11. An ultrasound data-processing system for determining information about a mechanical wave in heart tissue, comprising a processing system, configured to:
receive data representative of a time series of three-dimensional data frames, generated from ultrasound signals from a human or animal heart, wherein each frame comprises a set of voxels, each voxel of the frame having an acceleration value representative of an acceleration component of a respective location in the heart tissue at a common time;

identify, for each voxel in the series of frames, a frame of the series in which the acceleration value of the voxel is at a maximum;

generate a three-dimensional data set comprising a set of voxels corresponding to the voxels of the data frames, by assigning each voxel of the data set a time value representative of the time of the respective frame in the time series for which the acceleration value of the acceleration value of the corresponding voxel in the time series is at a maximum; and generate data representative of three-dimensional velocity vectors, which together provide a three-dimensional velocity vector field for the mechanical wave through the heart tissue, by calculating time derivatives along three orthogonal axes, wherein each respective three-dimensional velocity vector is determined from differences between the time value assigned to a respective voxel of the three-dimensional data set and time values assigned to voxels in a neighbourhood around the respective voxel.

12. The ultrasound data-processing system of claim 11, wherein the processing system is further configured to generate, from the three-dimensional velocity vector field, two-dimensional output data representing orientations of the three-dimensional velocity vector field and/or magnitudes of the three-dimensional velocity vector field.

13. The ultrasound data-processing system of claim 11, wherein the processing system is further configured to generate output data from the data representative of the three-dimensional velocity vector field, wherein generating the output data comprises reconstructing one or more trajectories from the data representative of three-dimensional velocity vector field and/or performing a vector field visualisation process.

14. The ultrasound data-processing system of claim 11, wherein the system further comprises a display, and wherein the processing system is further configured to:

generate image data from the data representative of the three-dimensional velocity vector field; and display the image data on the display.

15. The ultrasound data-processing system of claim 11, wherein the system further comprises an ultrasound probe, comprising an array of ultrasound transducers, and wherein the ultrasound probe and the processing system are configured for acquiring the time series of three-dimensional data frames.

16. The ultrasound data-processing system of claim 11, configured to generate the time series of three-dimensional data frames by:

receiving ultrasound signals reflected from the heart tissue;

generating a time series of three-dimensional Doppler data sets from the reflected ultrasound signals, wherein each three-dimensional Doppler data set represents velocities at locations in the heart tissue; and calculating the time derivatives of velocities within each three-dimensional Doppler data set.

17. The ultrasound data-processing system of claim 16, wherein the processing system is further configured to apply a clutter filter to each three-dimensional Doppler data set, wherein the clutter filter attenuates velocity values over a range of values that contains a velocity component of the mechanical wave.

18. The ultrasound data-processing system of claim 11, wherein the processing system is further configured to receive data representative of ultrasound images of the human or animal heart, acquired at a lower frame rate and/or higher spatial resolution than the time series of three-dimensional data frames, and to use the ultrasound images to perform a segmentation process.

19. The ultrasound data-processing system of claim 11, wherein the system further comprises an electrocardiogram (ECG) device, and wherein the processing system is further configured to use data generated by the ECG device to select the time series of three-dimensional data frames from a longer series of three-dimensional data frames.

20. A non-transitory computer-readable medium comprising software instructions which, when executed by a processing system, cause the processing system to:

receive data representative of a time series of three-dimensional data frames, generated from ultrasound signals from human or animal heart tissue, wherein each frame comprises a set of voxels, each voxel of the frame having an acceleration value representative of an acceleration component of a respective location in the heart tissue at a common time;

identify, for each voxel in the series of frames, a frame of the series in which the acceleration value of the voxel is at a maximum;

generate a three-dimensional data set comprising a set of voxels corresponding to the voxels of the data frames, by assigning each voxel of the data set a time value representative of the time of the respective frame in the time series for which the acceleration value of the corresponding voxel in the time series is at a maximum; and generate data representative of three-dimensional velocity vectors, which together provide a three-dimensional velocity vector field for the mechanical wave through the heart tissue, by calculating time derivatives along three orthogonal axes, wherein each respective three-dimensional velocity vector is determined from differences between the time value assigned to a respective voxel of the three-dimensional data set and time values assigned to voxels in a neighbourhood around the respective voxel.

21. The method of claim 1, comprising taking account of respective spatial resolutions of the three-dimensional data set along the three orthogonal axes when calculating the time derivatives along the three orthogonal axes.

22. The method of claim 1, further comprising determining one or more trajectories of the mechanical wave through heart tissue from the three-dimensional velocity vector field.

23. The method of claim 22, further comprising displaying the one or more trajectories so as to represent visually the propagation of the mechanical wave through the heart tissue.

* * * * *